United States Patent [19]

Iskander et al.

[11] 4,240,445
[45] Dec. 23, 1980

[54] ELECTROMAGNETIC ENERGY COUPLER/RECEIVER APPARATUS AND METHOD

[75] Inventors: Magdy F. Iskander, Midvale; Carl H. Durney, Salt Lake City, both of Utah

[73] Assignee: University of Utah, Salt Lake City, Utah

[21] Appl. No.: 954,054

[22] Filed: Oct. 23, 1978

[51] Int. Cl.³ .............................................. A61N 1/40
[52] U.S. Cl. .................. 128/804; 219/10.79; 336/66
[58] Field of Search ............... 128/804, 783, 800, 802, 128/653, 734; 219/10.79; 336/66

[56] References Cited

U.S. PATENT DOCUMENTS

| | | | |
|---|---|---|---|
| 2,529,914 | 11/1950 | Challener | 219/10.79 |
| 2,599,229 | 6/1952 | Bukaty | 219/10.79 |
| 2,655,589 | 10/1953 | Sorensen | 219/10.79 |
| 2,814,298 | 11/1957 | Argento | 128/804 X |
| 2,882,904 | 4/1959 | Rasmussen | 128/804 X |
| 3,077,195 | 2/1963 | Folsche | 128/804 |
| 3,228,030 | 1/1966 | Moore | 128/804 X |
| 3,437,778 | 4/1969 | Seulen et al. | 219/10.79 X |
| 3,462,336 | 8/1969 | Leatherman | 219/10.79 UX |
| 3,725,630 | 4/1973 | Gagliard | 219/10.79 |
| 4,119,102 | 10/1978 | LeVeen | 128/804 |

FOREIGN PATENT DOCUMENTS

| | | | |
|---|---|---|---|
| 1223965 | 9/1966 | Fed. Rep. of Germany | 128/804 |
| 1233947 | 10/1960 | France | 128/804 |
| 2236521 | 2/1975 | France | 128/804 |

*Primary Examiner*—Lee S. Cohen

[57] ABSTRACT

An apparatus and method for coupling electromagnetic energy into a dielectric material such as tissue while substantially reducing external leakage of the energy. The apparatus may also be used as a receiver for electromagnetic energy transmitted through tissue. The apparatus includes an open transmission line which is inherently non-radiating and may be configured with a centrally disposed, central strip conductor. A ground plane conductor is placed in spaced relationship to the central strip conductor and on both sides of the central strip conductor. Alternatively, the central strip conductor may be placed in spaced relationship to one side of a ground plane conductor. The central strip conductor is terminated with a resistor of resistance equal to the characteristic impedance of the open transmission line. The spacing and electrical geometry of each of the central strip conductor, ground plane conductor, electrical interconnection points, and the resistor are each selectively predetermined to minimize spurious radiation during coupling of the transmission apparatus. The method includes minimizing external leakage of electromagnetic energy while coupling electromagnetic energy with tissue using the apparatus of this invention.

8 Claims, 4 Drawing Figures

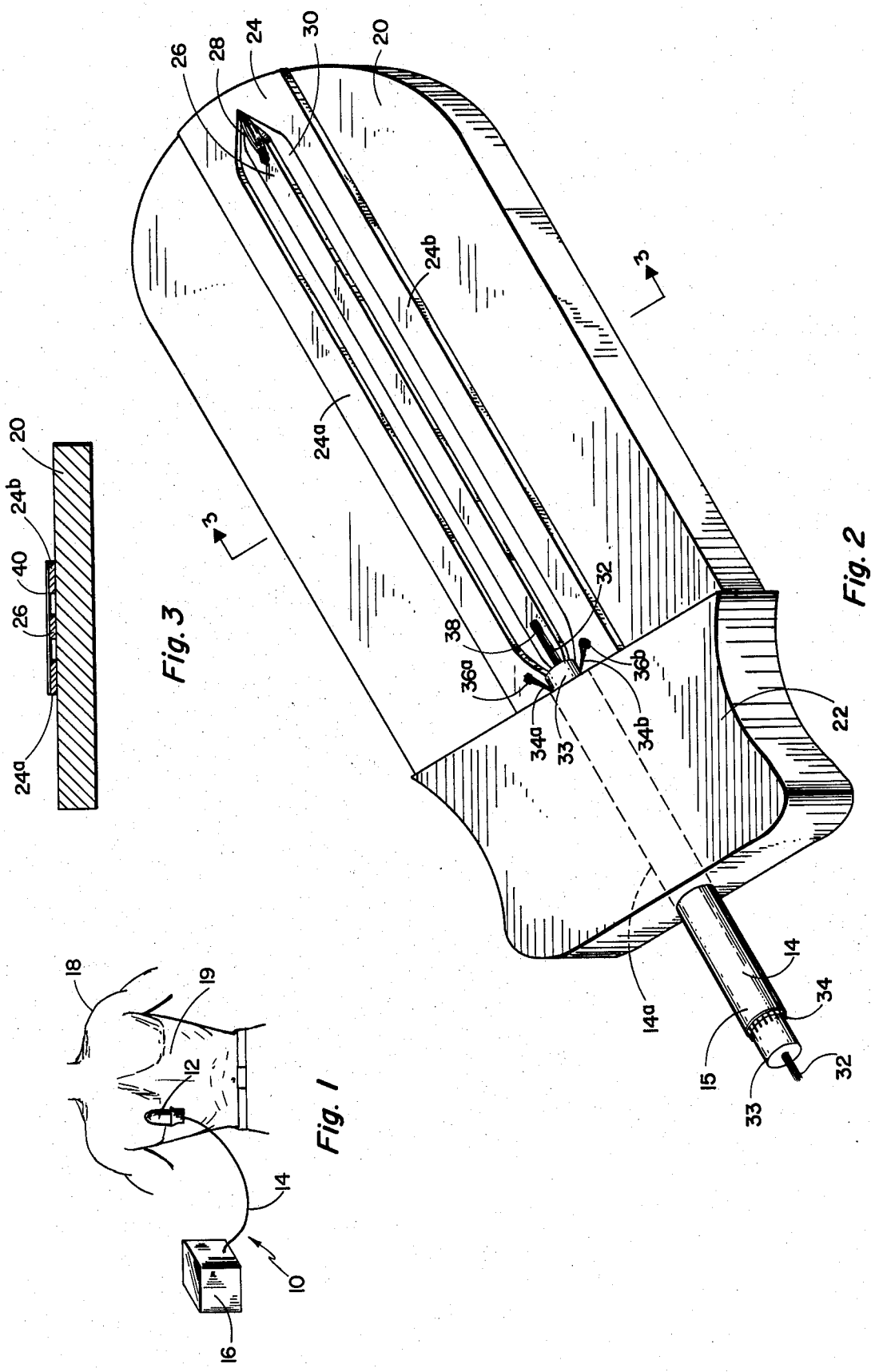

ELECTROMAGNETIC ENERGY COUPLER/RECEIVER APPARATUS AND METHOD

This invention was funded, in part and with appreciation, under a grant of the Department of Health, Education, and Welfare, the National Heart, Lung, Blood Institute Grant No. R01 HL20110-01.

BACKGROUND

1. Field of the Invention

This invention relates to electromagnetic applicators and, more particularly, to an electromagnetic transmission/receiver apparatus and method for directly coupling electromagnetic energy into a material with minimal external radiation.

2. The Prior Art

Recent statistics show that pulmonary and cardiopulmonary diseases are responsible for more than three million hospital admissions and 30,000 deaths every year in the United States. Pulmonary abnormalities are virtually always associated with changes in lung water content or distribution. Most workers agree that there is no single, nondestructive method available to detect accurately early changes in lung water content. Presently available techniques to measure such changes are generally insensitive, complicated, and clinically undesirable, particularly in detecting the important interstitial phase of acute pulmonary edema, before the onset of alveolar flooding, and before there is significant interference with gas exchange.

For a clinically useful technique, on the other hand, it is desirable to detect early changes in both the extravascular lung water, which strongly reflects most pulmonary abnormalities, and the intravascular compartment. Recently, the use of the electromagnetic methods to detect changes in lung water content have shown promising initial results, particularly for detecting small variations in water content. Particularly at microwave frequencies, changes in the dielectric properties of tissue are closely related to the amount of water present. Electromagnetic techniques, therefore, basically utilize changes in the permittivity and conductivity of the lung tissue to detect changes in lung water content. This method has the advantage of using highly penetrating electromagnetic signals rather than ultrasonic signals which are both highly attenuated and dispersed in the lung. Furthermore, electromagnetic techniques have the potential for continuous monitoring of patients in intensive care units, such as those with heart failure or extensive burns.

Before utilizing microwave or any other suitable electromagnetic energy method in clinical applications, the fundamental questions regarding its sensitivity, the possibility of developing a clinically adequate system to transmit and receive the signal, and its usefulness in monitoring changes as well as absolute values of lung water should be first carefully examined. An electromagnetic energy applicator that is adequate for clinical use should satisfy the following criteria:

1. It should be small, flat, and light-weight and hence convenient for placement on critically ill patients.
2. It should provide maximum coupling to the body with minimal external radiation, in order to minimize its sensitivity to the external surroundings.

These requirements, however, are difficult to satisfy in a radiation-type applicator such as the commonly used, open-ended waveguides and horns because of the associated radiation leakage. Furthermore, open-ended waveguides and horns tend to be too large at the operating frequency. Attempts to reduce the dimensions by using dielectric-loaded waveguides or to minimize the leakage by using flanged waveguides were found to be ineffectual because of the resulting excess weight and size.

It would, therefore, be an improvement in the art to provide a novel electromagnetic energy transmission/receiver apparatus and method for coupling electromagnetic energy into tissue while substantially reducing external leakage of the energy. It would also be an improvement in the art to provide a relatively small, flat, and light-weight electromagnetic energy transmission apparatus thereby rendering the applicator convenient for placement on critically ill patients. It would be a further improvement in the art to provide a method for minimizing external leakage of electromagnetic energy by coupling the electromagnetic energy into the tissue with an open transmission line. Such a novel apparatus and method is disclosed and claimed herein.

BRIEF SUMMARY AND OBJECTS OF THE INVENTION

The present invention relates to a novel electromagnetic energy transmission apparatus and method for coupling electromagnetic energy into a material or structure, including tissue, while substantially reducing external leakage of the electromagnetic energy. The apparatus includes an inherently non-radiating, open transmission line that accommodates coupling the electromagnetic energy into the tissue. The inherently non-radiating, open transmission line minimizes spurious radiation while coupling the energy into the tissue. Extraneous or spurious electromagnetic radiation from the applicator are reduced by carefully controlling the size, electrical-geometric configuration and placement of the various components in the apparatus.

It is, therefore, a primary object of this invention to provide improvements in electromagnetic energy apparatus.

Another object of this invention is to provide an improved method for coupling electromagnetic energy into a dielectric material.

Another object of this invention is to provide an improved electromagnetic energy coupling apparatus having relatively reduced dimensions and a relatively reduced profile.

Another object of this invention is to provide an improved method for coupling electromagnetic energy into tissue.

Another object of this invention is to reduce extraneous or spurious electromagnetic energy by selectively fabricating and designing the components and electrical interconnections of the apparatus according to conventional techniques.

Another object of this invention is to provide an improved apparatus and method for receiving electromagnetic energy transmitted through a dielectric material.

These and other objects and features of the present invention will become more fully apparent from the following description and appended claims taken in conjunction with the accompanying drawing.

BRIEF DESCRIPTION OF THE DRAWINGS

FIG. 1 is a schematic illustration of the electromagnetic energy apparatus of this invention shown in the environment of a schematically illustrated human torso;

FIG. 2 is an enlarged perspective view of a first preferred embodiment of a probe for the electromagnetic energy apparatus of this invention;

FIG. 3 is a cross section taken along lines 3—3 of FIG. 2 and includes an overlayment of dielectric material.

DETAILED DESCRIPTION OF THE PREFERRED EMBODIMENTS

Figure 4:
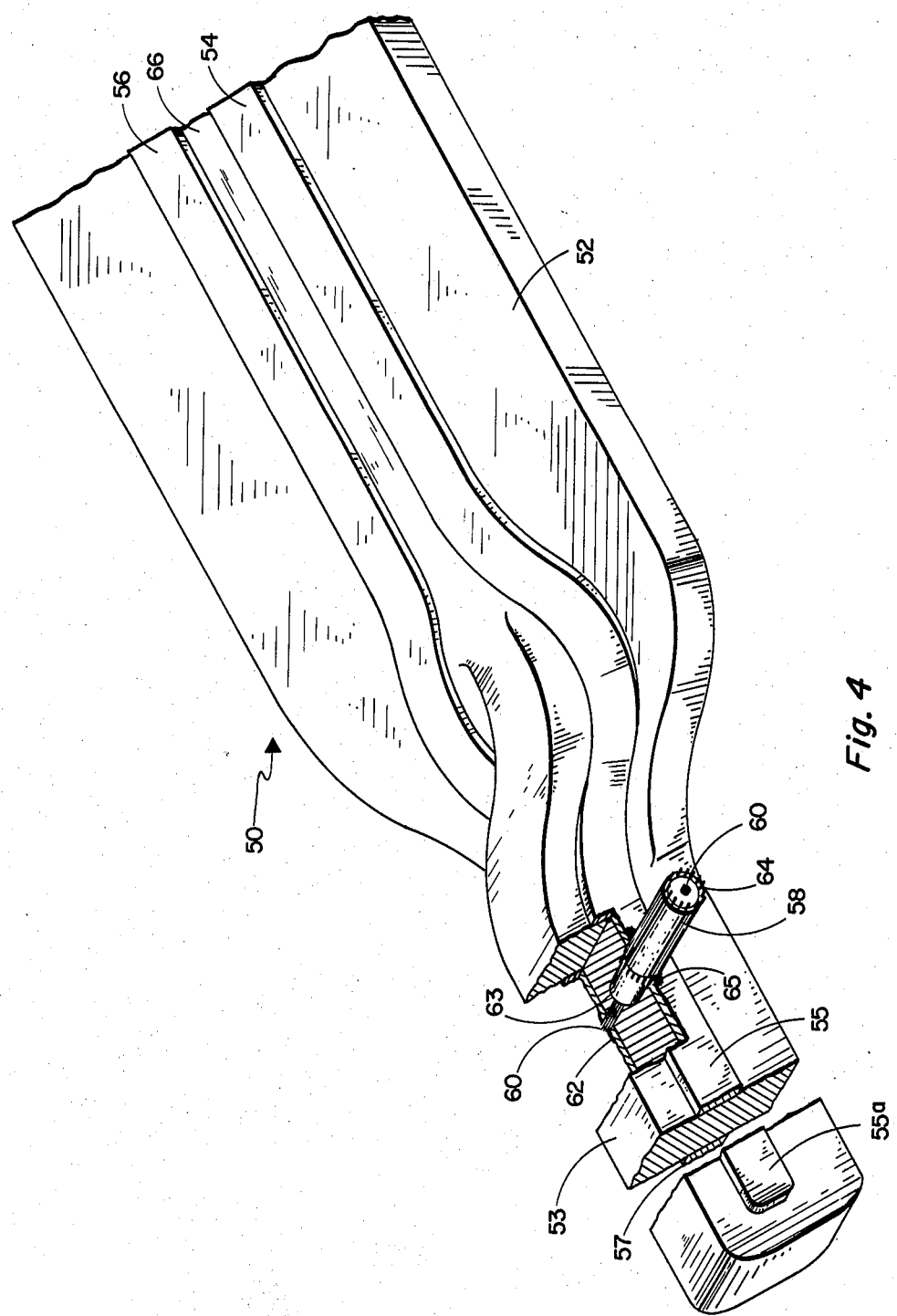
FIG. 4 is a perspective view of a second preferred embodiment of a probe for the electromagnetic energy apparatus of this invention with portions broken away for ease of illustration.

The invention is best understood by reference to the drawing wherein like parts are designated with like numerals throughout.

Referring now more particularly to FIG. 1, the electromagnetic energy apparatus of this invention is shown generally at 10 and includes a probe 12 coupled by coaxial cable 14 to a suitable electromagnetic energy source indicated schematically at 16. Probe 12 is shown placed against the chest 19 of a person 18 for the purpose of detecting lung water content as will be set forth more fully hereinafter. A corresponding probe (not shown) functions as a receiver/detector on the opposite side of chest 19. However, only one probe, probe 12, is shown herein for ease of illustration. Additionally, a plurality of probes 12 can be suitably positioned on chest 19 and the signals therefrom appropriately detected and/or received by other probes 12 with the various signals suitably cross correlated to provide the desired indication of the lung water condition of chest 19.

Referring now more particularly to FIG. 2, probe 12 is fabricated with a base 20 mounted to a handle 22 and having a central strip conductor 26 and a ground plane conductor 24 mounted thereon on each side of central strip conductor as indicated at 24a and 24b. Base 20 is fabricated from a suitable dielectric material such as plastic and sufficient thickness to inhibit coupling of electromagnetic energy from the reverse side of base 20. Preferably, base 20 is configured with a suitable flat profile to accommodate probe 12 being placed and/or taped against chest 19 (FIG. 1) for continuous monitoring of lung water changes.

Handle 22 serves primarily as an anchoring device for anchoring coaxial cable 14 as indicated in broken lines at 14a to prevent undue movement or breakage of the electrical connection between the electrical conductors in coaxial cable 14 with central strip conductor 26 and ground plane conductor 24. For example, coaxial cable 14 includes a center conductor 32 electrically connected to central strip conductor 26 at solder 38. Correspondingly, the shielding for coaxial cable 14 shown herein as wires 34 are suitably soldered to ground plane conductor at solder points 36a and 36b. The conventional center insulator 33 and external insulative sheath 15 suitably isolate each of center conductor 32 from grounding and/or contact with shielding conductor 34 or other undesirable contacts. It should be particularly noted that solder points 38, 36a and 36b are carefully prepared to minimize transition losses which would otherwise occur if there are sharp breaks or discontinuities "seen" by the wave propagated through the conductor apparatus of this invention.

Central strip conductor 26 is centrally disposed in a cutout 30 formed in the body of ground plane conductor 24. The appropriate ratio of the gap distance represented by gap 30 is maintained between central strip conductor 26 and ground plane conductor 24 in order to further reduce discontinuities which would tend to interrupt the wave pattern causing reflections and otherwise generating spurious signals. Central strip conductor 26 is terminated by a resistor 28 of resistance equal to the characteristic impedance of the open transmission line formed by central strip conductor 26 and ground plane conductor 24. In a presently preferred embodiment of this invention, resistor 28 was fabricated as a 50-ohm resistor by thin-film, metal deposition between central strip conductor 26 and ground plane conductor 24. Resistor 28 absorbs the waves travelling down central strip conductor 26 which would otherwise be reflected back thus creating standing waves.

In this first presently preferred embodiment of the present invention, probe 12 was fabricated from a convention printed circuit board. Printed circuit board is commercially available and includes a dielectric substrate with a layer of conductive material such as copper or the like deposited thereon by electrodeposition. In the matter of the present invention, probe 12 was prepared from a printed circuit board by etching the extraneous metallic deposition from base 20 thereby leaving ground plane conductor 24 and central strip conductor 26. Accordingly, probe 12 was prepared as a relatively small, flat, light-weight probe to accommodate convenient placement on critically ill patients. The surprising performance of probe 12 was verified by mapping the fields coupled through a layer of wet sponge. Wet sponge was used to simulate tissue and was place so as to induce fields in the sponge from the field formed around central strip conductor 26 and ground plane conductor 24. The fields were measured using a conventional H-sonde antenna as a pickup or detector. Alternatively, a second probe 12 could easily serve as the necessary detector/receiver.

The importance of minimizing radiation leakage from probe 12 is clearly demonstrated by the fact that there is about a 60 db signal attenuation in a human thorax. Accordingly, even a weak signal will undesirably mask the transmitted signal through the thorax. It is, therefore, clear from the foregoing that the appropriate coupling of the electromagnetic energy into tissue without appreciable leakage is extremely important. Experimentally probe 12 was used as a microwave applicator in several experiments involving the artificial inducement of pulmonary edema in experimental animals according to prescribed test procedures. The status of the pulmonary edma was monitored with serial, lateral chest radiograpshs and also by monitoring of the parameters (a) systemic arterial pressure, (b) mean pulmonary arterial pressure, (c) mean left arterial pressure (or mean pulmonary venous pressure), and (d) cardiac output. The magnitude and phase of the microwave transmission coefficient were also recorded during the course of the experiments. X-rays were used to monitor any changes in the relative positions of the applicators.

The results obtained from several experiments demonstrated various promising features of the method of this invention. In particular, it was clearly demonstrated that electromagnetic measurements responded quickly to the initial stages of artifically induced pulmonary edema. There was found to be a good correlation between the changes in the phase of the transmissin coefficient and the pulmonary arterial pressure, which pressure is assumed to be a good indicator of the state of edema. For example, it was found that a phase change of more than 150° was recorded after infusing 650 cc of blood into the femoral vein of the animal. Similar phase changes were also recorded upon reversing the process by withdrawing blood from the animal. It was found that the applicator and receiver caused minimal external radiation and that excellant measuremwent of signals transmitted through the thorax of the animal was obtained.

As far as the optimum operating frequency is concerned, a tradeoff between the magnitude and phase of the transmission coefficient was observed. Based upon a planar model analysis, it was found that with a frequency increase the attenuation through the thorax increased and the phase sensitivity also increased. Therefore, for better phase resolution, it was desirable to operate at higher frequencies. For a man-size model it was found that to maintain the attenuation constant within the resolution of a commerically available network analyzer, an upper frequency limit of 1.5 GHz is essential. This limit also takes into account about 20 dB attenuation as a result of the mismatch between both the transmitting and receiving applicators and the chest wall. As far as the phase is concerned, a one degree change for every 1% change in lung water was taken as a criterion for the lower frequency limit. On this basis, a frequency of 740 MHz was found to be a lower frequency limit. Hence, for a man-size model, the optimum frequency band is between 740 MHz and 1.5 GHz. Obviously, the 915 MHz allocated for medical use the Federal Communications Commission is in the optimum band.

In addition to detecting lung water content, it has also been proposed to use electromagnetic energy, possibly in the microwave spectrum, for hyperthermia applications. The energy is used to increase the temperature of certain malignant tissues. Increased temperature of these tissues has been found to increase their sensitivity to destruction by x-ray.

Referring now more particularly to FIG. 3, a cross sectional view is taken through base 20 further illustrating the interrelationship between central strip conductor 26 and ground plane conductor 24 and, more particularly, to the two portions 24a and 24b of ground plane conductor 24. While the overall widths of ground plane conductor 24, conductors 24a and 24b thereof, are of reduced importance, the width of central strip conductor 26 and the distances between the conductors in addition to the ratios of the distances and widths are important to provide a smooth, continuous wave propagation therethrough. FIG. 3 differs from FIG. 2 by including a dielectric overlayment 40 across central strip conductor 26 and ground plane conductor 24. Overlayment 40 is chosen from a lossless dielectric material having permittivity similar to that of tissue in order to more suitably absorb hot spots which might otherwise occur upon coupling of relatively high electromagnetic energy into the tissue, particularly at the interface between the tissue and the conductors. While the apparatus and method of this invention will operate without overlayment 40, it is believed that overlayment 40 contributes a limited degree of safety to the apparatus and method of this invention, particularly where tissue is involved.

Referring now more particularly to FIG. 4, a second preferred embodiment of the transmission apparatus of this invention is shown as a probe 50 and includes a first conductor 56 placed in juxtaposition with a second conductor 54 on a suitable dielectric substrate, base 52. A gap 66 between first conductor 56 and second conductor 54 is suitably preconfigured to provide the desired gap distance. Additionally, first conductor 56 is terminated with a resistor (not shown) having a resistance equal to the characteristic impedance of the transmission line formed by first conductor 56 and second conductor 54.

Base 52 is suitably contoured with a desirable curvilinear configuration into a vertical, planar handle 53. Handle 53 is fabricated as an integral part of base 52 and serves the primary function of providing a smooth electrical transition for the electrical conductors in coaxial cable 58 with first conductor 56 and second conductor 54. For example, coaxial cable 58 intersects handle 53 at right angles for the purpose of providing a smooth transition between the conductors within coaxial cable 58 and the corresponding conductors on base 52. Center conductor 60 of coaxial cable 58 passes through handle 53 and is shielded from second conductor 54 by insulation 63 where it is electrically interconnected with first conductor 56 at solder 62. The sheath or shielding wire 64 surrounding insulative layer 63 is electrically connected to second conductor 54 at solder 65. Importantly, in each instance care is taken in solder points 62 and 65 to assure a smooth transistion for the purpose of minimizing spurious radiation. Additional stability between coaxial cable 58 and handle 53 may be provided by an appropriate anchor (not shown) to secure the interconnection between coaxial cable 58 and the electrical components of probe 50.

Second conductor 54 terminates on handle 53 in a second conductor extension 55 while first conductor 56 terminates in a first condcutor extension 57 on the opposite face of handle 53. Importantly, a smooth curvilinear profile is provided for the transistion between second conductor extension 55 and second conductor 54 and correspondingly, between first conductor extension 57 and first conductor 56 thereby minimizing transmission losses which would otherwise occur, creating spurious radiation signals.

Impedance matching for second conductor extension 55 and first conductor extension 57 is provided by appropriately adjusting the length thereof as indicated schematically herein at 55a thereby assuring the appropriate wave propagation down the open transmission line formed by first conductor 56 and second conductor 54.

Coupling of the electromagnetic energy into tissue (not shown) by probe 50 is accomplished by bringing probe 50 and, more particularly, the field created between first conductor 56 and second conductor 54, near the tissue thereby allowing the tissue to intersect the field so that another field is induced into the tissue. If desired, an appropriate dielectric substrate such as overlayment 40 (FIG. 3) may be placed across first conductor 56 and second conductor 54 to minimize hot spots which may otherwise occur at points of contact with the tissue and relatively high electromagnetic energy levels.

The foregoing description is concerned primarily with coupling electromagnetic energy into tissue. Clearly, of course, the apparatus and method of this invention may also find suitable uses in other fields including, for example, microwave imaging, microwave radiometers, and the like.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All claims that come within the meaning and range of equivalency of the claims are to be embraced within their scope.

What is claimed and desired to be secured by a United States Letters Patent is:

1. An apparatus for coupling electromagnetic energy into a material comprising:
    a substrate body of dielectric material, the body having an external surface;
    an open transmission line mounted at the external surface of the dielectric substrate to accommodate access to electromagnetic fields adjacent the open transmission line, the open transmission line serving as an inducing means for inducing electromagnetic energy into the material and comprising a central strip conductor and a ground plane conductor, the central strip conductor being surrounded in spaced relationship by the ground plane conductor, the open transmission line further comprising a resistor electrically interconnecting the central strip conductor and the ground plane conductor; and
    means for connecting the open transmission line with a source of electrical energy to thereby allow the open transmission line to operate as an inducing means.

2. The apparatus defined in claim 1 wherein the open transmission line comprises a predetermined spatial relationship between the central strip conductor and the ground plane conductor, the spatial relationship being selectively predetermined for smooth wave propagation with reduced transition losses.

3. An apparatus for coupling electromagnetic energy into a material comprising:
    a substrate body of dielectric material, the body having an external surface, the dielectric substrate further comprising handle means for handling the apparatus;
    an open transmission line mounted at the external surface of the dielectric substrate to accommodate access to electromagnetic fields adjacent the open transmission line, the open transmission line serving as an inducing means for inducing electromagnetic energy into the material and comprising a central strip conductor and a ground plane conductor, the central strip conductor being surrounded in spaced relationship by the ground plane conductor, the open transmission line further comprising a resistor electrically interconnecting the central strip conductor and the ground plane conductor; and
    means for connecting the open transmission line with a source of electrical energy to thereby allow the open transmission line to operate as an inducing means.

4. The apparatus defined in claim 3 wherein the means for connecting the open transmission line with a source of electrical energy further comprises a coaxial cable electrically connected with the central strip conductor and the ground plane conductor, the handle means serving as a stabilizing means for the coaxial cable.

5. The apparatus defined in claim 3 wherein the central strip conductor and the ground plane conductor further comprise an overlayment, the overlayment having dielectric properties similar to the material to enhance electromagnetic coupling when the open transmission line is placed adjacent the material.

6. A method for coupling electromagnetic energy to a dielectric material comprising:
    fabricating an open transmission line for electromagnetic energy by obtaining a body of dielectric substrate having a surface and mounting the open transmission line at the surface of the body of dielectric substrate, the open transmission line comprising a central strip conductor mounted at the surface of the body of dielectric substrate and surrounded in spaced relationship by a ground plane conductor mounted at the surface of the body of dielectric substrate and a resistor electrically interconnecting the central strip conductor with the ground plane conductor;
    interconnecting the open transmission line with a source of electromagnetic energy; and
    coupling the electromagnetic energy into the dielectric material by bringing the open transmission line into at least close proximity with the dielectric material thereby inducing electromagnetic fields in the dielectric material.

7. A microwave coupler for coupling microwave energy to tissue comprising:
    a dielectric substrate configured with a surface adapted to be placed against the tissue;
    an open transmission line mounted to the surface of the dielectric substrate, the open transmission line comprising a central strip conductor, a ground plane conductor, and a resistor, the central strip conductor being surrounded in spaced relationship by the ground plane conductor and electrically interconnected to the ground plane conductor by the resistor; and
    means for connecting the open transmission line to a source of electromagnetic energy, the electromagnetic energy inducing microwave energy in the open transmission line.

8. A method for coupling microwave energy into tissue comprising:
    forming a microwave applicator as an open transmission line by placing a first conductor on a dielectric substrate as a central strip conductor and mounting a second conductor on the dielectric substrate as a ground plane conductor, the ground plane conductor in spaced relationship and electrically interconnecting the central strip conductor with the ground plane conductor with a resistor;
    interconnecting the open transmission line with a source of electromagnetic energy, the electromagnetic energy inducing microwave energy with the open transmission line; and
    coupling the microwave energy into the tissue by bringing the microwave applicator into proximity with the tissue thereby inducing fields in the tissue.

* * * * *